(12) United States Patent
Pu et al.

(10) Patent No.: US 10,413,431 B2
(45) Date of Patent: Sep. 17, 2019

(54) REHABILITATION SYSTEM WITH STIFFNESS MEASUREMENT

(71) Applicant: NATIONAL TSING HUA UNIVERSITY, Hsinchu (TW)

(72) Inventors: Shu-Wei Pu, Taichung (TW); Jen-Yuan Chang, Hsinchu County (TW)

(73) Assignee: NATIONAL TSING HUA UNIVERSITY, Hsinchu (TW)

( * ) Notice: Subject to any disclaimer, the term of this patent is extended or adjusted under 35 U.S.C. 154(b) by 1178 days.

(21) Appl. No.: 14/663,985

(22) Filed: Mar. 20, 2015

(65) Prior Publication Data
US 2016/0193101 A1    Jul. 7, 2016

(30) Foreign Application Priority Data
Jan. 5, 2015 (TW) .............................. 104100119 A

(51) Int. Cl.
*A61H 1/02* (2006.01)
*A61F 2/70* (2006.01)

(52) U.S. Cl.
CPC .............. *A61F 2/70* (2013.01); *A61H 1/0288* (2013.01); *A61F 2002/704* (2013.01); *A61H 2201/1215* (2013.01); *A61H 2201/1276* (2013.01); *A61H 2201/149* (2013.01); *A61H 2201/1436* (2013.01); *A61H 2201/165* (2013.01); *A61H 2201/5007* (2013.01); *A61H 2201/5023* (2013.01); *A61H 2201/5058* (2013.01); *A61H 2201/5061* (2013.01); *A61H 2205/067* (2013.01)

(58) Field of Classification Search
CPC ...... A61H 1/02; A61H 1/0285; A61H 1/0288; A61B 34/71; A61F 2/586; A61F 2002/5093; A61F 2002/7635; B25J 9/104; B25J 9/1045; B25J 15/0009; B66D 2700/026
See application file for complete search history.

(56) References Cited

U.S. PATENT DOCUMENTS

| | | | | |
|---|---|---|---|---|
| 4,921,293 A | * | 5/1990 | Ruoff | A61F 2/583 294/106 |
| 5,092,645 A | * | 3/1992 | Okada | B25J 13/085 294/119.1 |
| 5,373,747 A | * | 12/1994 | Ogawa | B25J 13/084 73/862.041 |
| 5,631,861 A | * | 5/1997 | Kramer | G06F 3/011 414/5 |
| 5,912,658 A | * | 6/1999 | Bergamasco | B25J 9/0006 345/156 |
| 6,537,237 B1 | * | 3/2003 | Hopkins | A61F 5/0125 602/16 |

(Continued)

*Primary Examiner* — Rachel T Sippel
*Assistant Examiner* — Christopher E Miller
(74) *Attorney, Agent, or Firm* — Muncy, Geissler, Olds & Lowe, P.C.

(57) ABSTRACT

A rehabilitation system with stiffness measurement on a body part to be rehabilitated is disclosed. The rehabilitation system includes a rehabilitation unit and a processor. The rehabilitation unit includes an exoskeleton brace holding a rehabilitation part of user and traction lines driving the exoskeleton brace for moving. When the exoskeleton brace moves, the processor analyzes tensions of the traction lines to obtain stiffness information relating to the rehabilitation part of user.

7 Claims, 10 Drawing Sheets

(56) References Cited

U.S. PATENT DOCUMENTS

| | | | | |
|---|---|---|---|---|
| 8,056,423 B2* | 11/2011 | Abdallah | ............... | B25J 9/1045 73/826 |
| 2006/0094989 A1* | 5/2006 | Scott | ............... | A61F 2/54 601/5 |
| 2006/0167564 A1* | 7/2006 | Flaherty | ............... | A61B 5/0476 623/57 |
| 2008/0000317 A1* | 1/2008 | Patton | ............... | A61F 5/0102 74/500.5 |
| 2010/0041521 A1* | 2/2010 | Ingvast | ............... | A61H 1/0288 482/49 |
| 2010/0152898 A1* | 6/2010 | Reiland | ............... | B25J 9/1633 700/261 |
| 2010/0249676 A1* | 9/2010 | Kawakami | ............... | A61F 5/013 601/40 |
| 2010/0280662 A1* | 11/2010 | Abdallah | ............... | H01R 13/17 700/261 |
| 2011/0130879 A1* | 6/2011 | Abdallah | ............... | B25J 9/1615 700/260 |
| 2012/0029399 A1* | 2/2012 | Sankai | ............... | A61B 5/04888 601/40 |
| 2012/0150322 A1* | 6/2012 | Goldfarb | ............... | A61F 2/583 623/63 |
| 2012/0157263 A1* | 6/2012 | Sivak | ............... | G06F 3/014 482/4 |
| 2013/0226350 A1* | 8/2013 | Bergelin | ............... | B25J 9/0006 700/275 |
| 2014/0172166 A1* | 6/2014 | Kim | ............... | B25J 3/04 700/259 |
| 2015/0165621 A1* | 6/2015 | Ko | ............... | B25J 9/104 74/490.04 |
| 2015/0173993 A1* | 6/2015 | Walsh | ............... | A61H 1/024 414/4 |
| 2015/0342818 A1* | 12/2015 | Ikebe | ............... | A61H 1/0288 601/40 |
| 2015/0352725 A1* | 12/2015 | Santos | ............... | B25J 9/1045 74/490.05 |
| 2015/0374575 A1* | 12/2015 | Kamper | ............... | A61H 1/0288 601/40 |

\* cited by examiner

REHABILITATION SYSTEM WITH STIFFNESS MEASUREMENT

CROSS-REFERENCE TO RELATED APPLICATION

This application claims priority from Taiwan Patent Application No. 104100119, filed on Jan. 5, 2015, in the Taiwan Intellectual Property Office, the content of which are hereby incorporated by reference in their entirety for all purposes.

BACKGROUND OF THE INVENTION

1. Field of the Invention

This application relates to a rehabilitation system, and more particularly, to a rehabilitation system with stiffness measurement function.

2. Description of the Related Art

With the advent of an aging society, the symptoms such as a stroke, the inconvenience of action due to a heart attack, paralysis, and so on often occur in the surrounding. On the other hand, cases of the physical disability resulted from car accidents and other injuries are endless. As far as the patients are concerned, the treatment comes with the lengthy rehabilitation, and this rehabilitation process is usually carried with the specific rehabilitation equipment.

However, when the rehabilitation equipment is used to carry out the rehabilitation, the patient's recovery can be assessed according to the experiences of physician or the patient him/herself. The physical recovery of patient is roughly estimated on the basis of the rehabilitation activities and lacks of a system to accurately quantify the conditions of the rehabilitation. In addition, thanks to the inter-individual difference of the patient's body conditions, the heuristic rule may tend to be subjective and cause false positives. Therefore, establishing a rehabilitation system to provide physicians or the patients with the quantitative targets for rehabilitation activities is necessary.

SUMMARY OF THE INVENTION

In view of the aforementioned technical problems, the objective of the present invention provides a rehabilitation system with stiffness measurement function which provides the physician or the patient with the quantitative targets for assessing the recovery of the rehabilitation.

According to one objective of the present invention, a rehabilitation system with stiffness measurement function is provided. The rehabilitation system includes a rehabilitation unit and a processor. The rehabilitation unit includes an exoskeleton brace coupled to a rehabilitation part of a user, a first traction line coupled to an end of the exoskeleton brace, a second traction line coupled to the end of the exoskeleton brace, a first tension measurement member configured to enable the first traction line to pass therethrough, a second tension measurement member configured to enable the second traction line to pass therethrough, and a driving motor coupled to the first traction line and the second traction line. When the driving motor rotates in a first driving direction, the exoskeleton brace is driven by the first traction line to move in a first direction, and when the driving motor rotates in a second driving direction, the exoskeleton brace is driven by the second traction line to move in a second direction opposite to the first direction. The processor is electrically connected to the first tension measurement member and the second tension measurement member. When the exoskeleton brace of the rehabilitation unit moves, the first tension measurement member and the second tension measurement member measure a first tension in the first traction line and a second tension in the second traction line, respectively. The first tension measurement member and the second tension measurement member provide the first tension and the second tension to the processor, and the processor analyzes the first tension and the second tension to obtain stiffness information of the rehabilitation part in a specific moving direction.

Preferably, the first tension measurement member may include a first roller, a second roller, and a third roller. The first traction line may be disposed at a first side of the first roller and the third roller and a second side opposite to the first side of the second roller. The second roller may be coupled to a cantilever beam with a strain gauge to measure the first tension in the first traction line. The strain gauge may output a tension signal relating to the first tension to the processor.

Preferably, the strain gauge may include a first gauge resistor and a second gauge resistor, and the first gauge resistor and the second gauge resistor may be coupled to a bridge circuit to obtain the tension signal relating to the first tension.

Preferably, the rehabilitation system may further include a plurality of the rehabilitation units. The exoskeleton brace of each of the rehabilitation units includes a plurality of joints, and the first tension measurement member and the second tension measurement member of each of the rehabilitation units are electrically connected to the processor.

Preferably, the rehabilitation system may further include a motion capture glove electrically connected to the processor and outputting a motion signal to the processor. The processor may be electrically connected to the driving motor of each of the rehabilitation units and control the driving motor of each of the rehabilitation units according to the motion signal.

Preferably, the processor may store unload data measured when the exoskeleton brace is not coupled to the rehabilitation part, and the processor may compare the first tension and the second tension with the unload data to obtain the stiffness information of the rehabilitation part in the specific moving direction.

Preferably, the processor may further store a tension database corresponding to a tension variety in the first traction line and the second traction line at various situations of stiffness, and the processor may analyze the first tension and the second tension by table look-up or interpolation according to the upload data and the tension database to obtain the stiffness information of the rehabilitation part in the specific moving direction.

Preferably, the processor may include a storing space, and the measured stiffness information of the rehabilitation part in the specific moving direction may be stored in the storing space.

Preferably, the rehabilitation system may further include a display electrically connected to the processor, receiving the stiffness information from the processor, and presenting information relating to the stiffness information.

As mentioned above, a rehabilitation system with stiffness measurement function in accordance with the present invention may have one or more advantages as follows.

1. A rehabilitation system with stiffness measurement function in accordance with the present invention is able to analyze the tension on the traction line which drives the exoskeleton brace to thereby obtain the stiffness information of the rehabilitation part.

2. A rehabilitation system with stiffness measurement function in accordance with the present invention is able to analyze the stiffness information of the rehabilitation part by directly measuring the tension so as to reduce errors of the system resulted from interference or other signals.

3. By means of the plurality of the rehabilitation units, and the exoskeleton braces of each of the rehabilitation units including a plurality of joints, a rehabilitation system with stiffness measurement function in accordance with the present invention is able to correspond to the human body where complicated activities can be performed, such as the hands.

4. A rehabilitation system with stiffness measurement function in accordance with the present invention may include a motion capture glove, thereby to drive the exoskeleton brace mounted on another side of body through the reflected action signal, so as to perform more sophisticated rehabilitation activities.

5. By means of the display, a rehabilitation system with stiffness measurement function in accordance with the present invention is able to instantly display messages concerning the stiffness function such that the physician or the patient is able to obtain the messages by the display.

BRIEF DESCRIPTION OF THE DRAWINGS

Hereinafter, embodiments of the present invention will be described in detail with reference to the accompanying drawings so that those skilled in the art to which the present invention pertains can realize the present invention, wherein.

DETAILED DESCRIPTION OF THE PREFERRED EMBODIMENTS

Hereinafter, embodiments of the present invention will be described in detail with reference to the accompanying drawings so that those skilled in the art to which the present invention pertains can realize the present invention. As those skilled in the art would realize, the described embodiments may be modified in various different ways, all without departing from the spirit or scope of the present invention.

Figure 1:
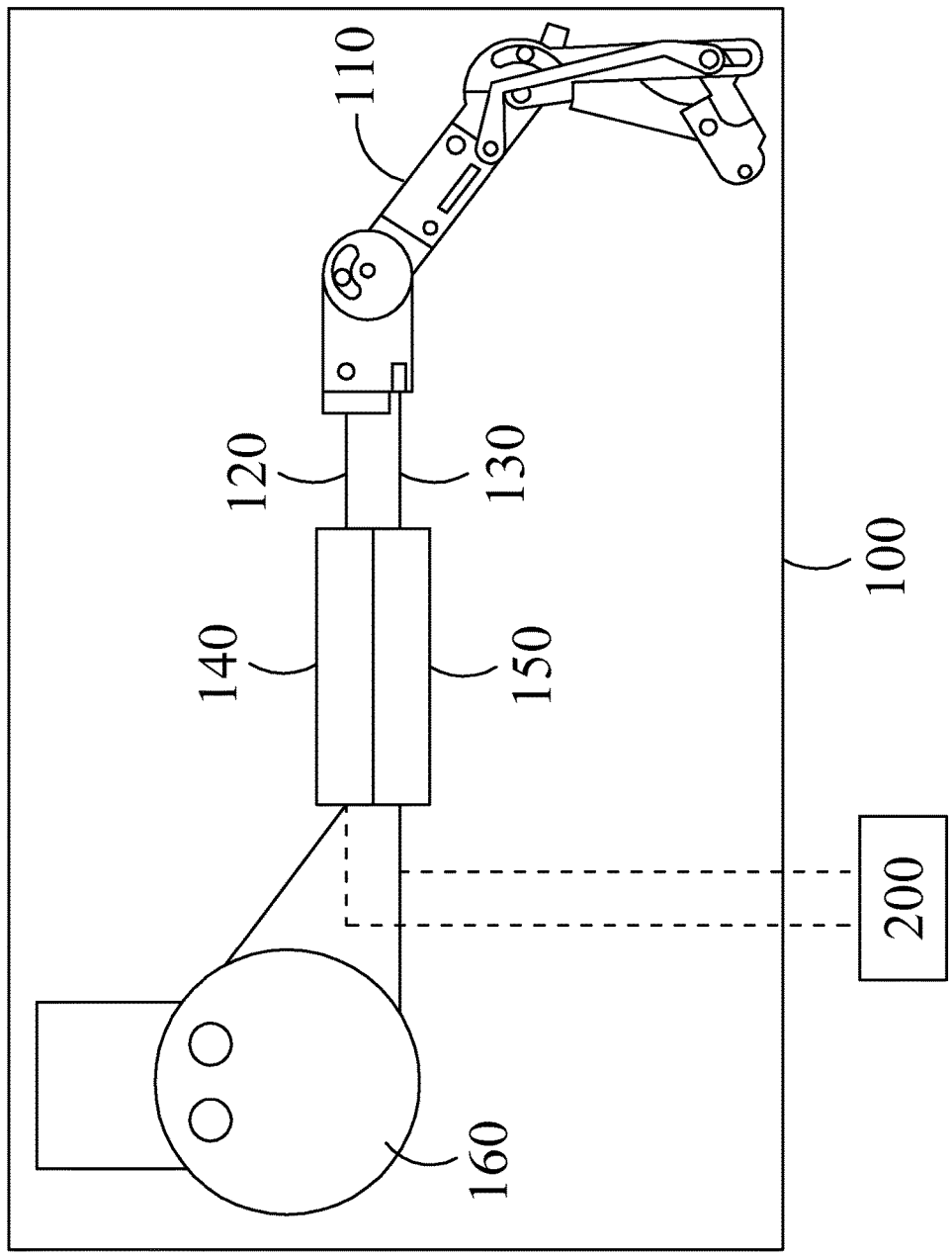
FIG. 1 is a schematic diagram of the first embodiment of a rehabilitation system in accordance with the present invention.

Please refer to FIG. 1 which is a schematic diagram of the first embodiment of a rehabilitation system in accordance with the present invention. As shown in the figure, a rehabilitation system with stiffness measurement function in accordance with the present invention includes a rehabilitation unit 100 and a processor 200. The rehabilitation unit 100 includes an exoskeleton brace 110 coupled to a rehabilitation part of a user, a first traction line 120 coupled to an end of the exoskeleton brace 110, a second traction line 130 coupled to the end of the exoskeleton brace 110, a first tension measurement member 140 configured to enable the first traction line 120 to pass therethrough, a second tension measurement member 150 configured to enable the second traction line to pass therethrough, and a driving motor 160 coupled to the first traction line 120 and the second traction line 130. When the driving motor 160 rotates in a first driving direction, the exoskeleton brace 110 is driven by the first traction line 120 to move in a first direction, and when the driving motor 160 rotates in a second driving direction, the exoskeleton brace 110 is driven by the second traction line 130 to move in a second direction opposite to the first direction. The processor 200 is electrically connected (the chain lines shown in FIG. 1 denotes the connection) to the first tension measurement member 140 and the second tension measurement member 150 of the rehabilitation unit 100. When the exoskeleton brace 110 of the rehabilitation unit 100 moves, the first tension measurement member 140 and the second tension measurement member 150 measure a first tension in the first traction line 120 and a second tension in the second traction line 130, respectively, and the processor 200 thereby analyzes the first tension and the second tension to obtain stiffness information of the rehabilitation part in a specific moving direction.

Specifically, the exoskeleton brace 110 of the rehabilitation unit 100 of a rehabilitation system with stiffness measurement function in accordance with the present invention is coupled to the user's rehabilitation part, such as the patient's body joints which need for rehabilitation. The exoskeleton brace 110 is driven by traction line. That is to say, as shown in FIG. 1, ends of the first traction line 120 and the second traction line 130 are respectively coupled to a top end of the exoskeleton brace 110, and the other ends of the first traction line 120 and the second traction line 130 are respectively coupled to the driving motor 160. The driving motor 160 may be a servo motor, and the driving motor 160 is able to receive incoming signals to precisely control the position and condition of the exoskeleton brace 110 via the first traction line 120 and the second traction line 130 coupled to the driving motor 160. For example, when the driving motor 160 shown in FIG. 1 is rotating counterclockwise, the first traction line 120 fixed on the driving motor 160 is pulled towards the driving motor 160 so as to drive the exoskeleton brace 110 to stretch. When the driving motor 160 shown in FIG. 1 is rotating clockwise, the second traction line 130 fixed on the driving motor 160 is pulled towards the driving motor 160 so as to drive the exoskeleton brace 110 to bend. Because the exoskeleton brace 110 is coupled to the patient's rehabilitation part, when the exoskeleton brace 110 is moving, it also drives the patient's rehabilitation part moving in a specific direction, so as to achieve the effect of rehabilitation.

The rehabilitation system with stiffness measurement function in accordance with the present is able to measure a tension variety in the first traction line 120 and the second traction line 130 while the driving motor 160 is driving the exoskeleton brace 110. Specifically, a rehabilitation system with stiffness measurement function in accordance with the present further includes a first tension measurement member 140 and a second tension measurement member 150. The first tension measurement member 140 is configured to enable the first traction line 120 to pass therethrough, and the second tension measurement member 150 is configured to enable the second traction line 130 to pass therethrough. Thus, when the drive motor 160 applies a force to the first traction line 120 and the second traction line 130 to drive the exoskeleton brace 110, the tension in the first traction line 120 and the second traction line 130 varies. The tension variety is related to the various situations of the stiffness of the patient's rehabilitation part in the specific direction. That is as previously described, the patient's rehabilitation part can be driven in the specific direction by the cooperation of the driving motor 160, and the first traction line 120, the second traction line 130 and the exoskeleton brace 110. Regarding this specific direction of motion, when the rehabilitation part coupled to the exoskeleton brace 110 has various situations of stiffness, even the force output by the driving motor 160 is equivalent, the tensions reacted in the first traction line 120 and the second traction line 130 are different. Thus, the first tension measurement member 140 and the second tension measurement member 150 of the present invention are able to lead the first traction line 120 and the second traction line 130, and measure the tension on the first traction line 120 and the second traction line 130 simultaneously. Afterwards, the tension information is transmitted to the processor 200, and when the tension information is received, the processor 200 calculates the stiffness information of the patent's rehabilitation part in the specific direction by analyzing the tension information. The calculated stiffness information is provided to the physician or the patent as the quantitative targets for assessing the patient's health condition. The processor 200 may be the computer or circuit having general calculation function, but shall not be limited thereto.

The method of analyzing the various situations of stiffness by the tension applied in the present invention also has the following advantage. Generally, when a driving device which is similar to servo motor is used, a feedback of the driven object is derived from an electronic feedback signal of the driving device given by the driven object. Such feedback signals may be affected by the errors caused by the electronic system itself, or other electronic signal interference, resulting that the feedback derived from the driven object is erroneous. For example, the angle of the reconfigured rotor of a maintained motor may vary slightly with the original one, and thus, the received feedback signal may cause errors while being interpreted. However, the present invention applies the tension to analyze the various situations of stiffness of the rehabilitation part that is equivalent to the directly measurement of the source of the tension variety. Hence, errors resulted from the above-described configuration of the system, or other electronic signals can be avoided. As a result, the present invention can achieve a very high accuracy concerning the stiffness measurement of the rehabilitation part.

Figure 2A:
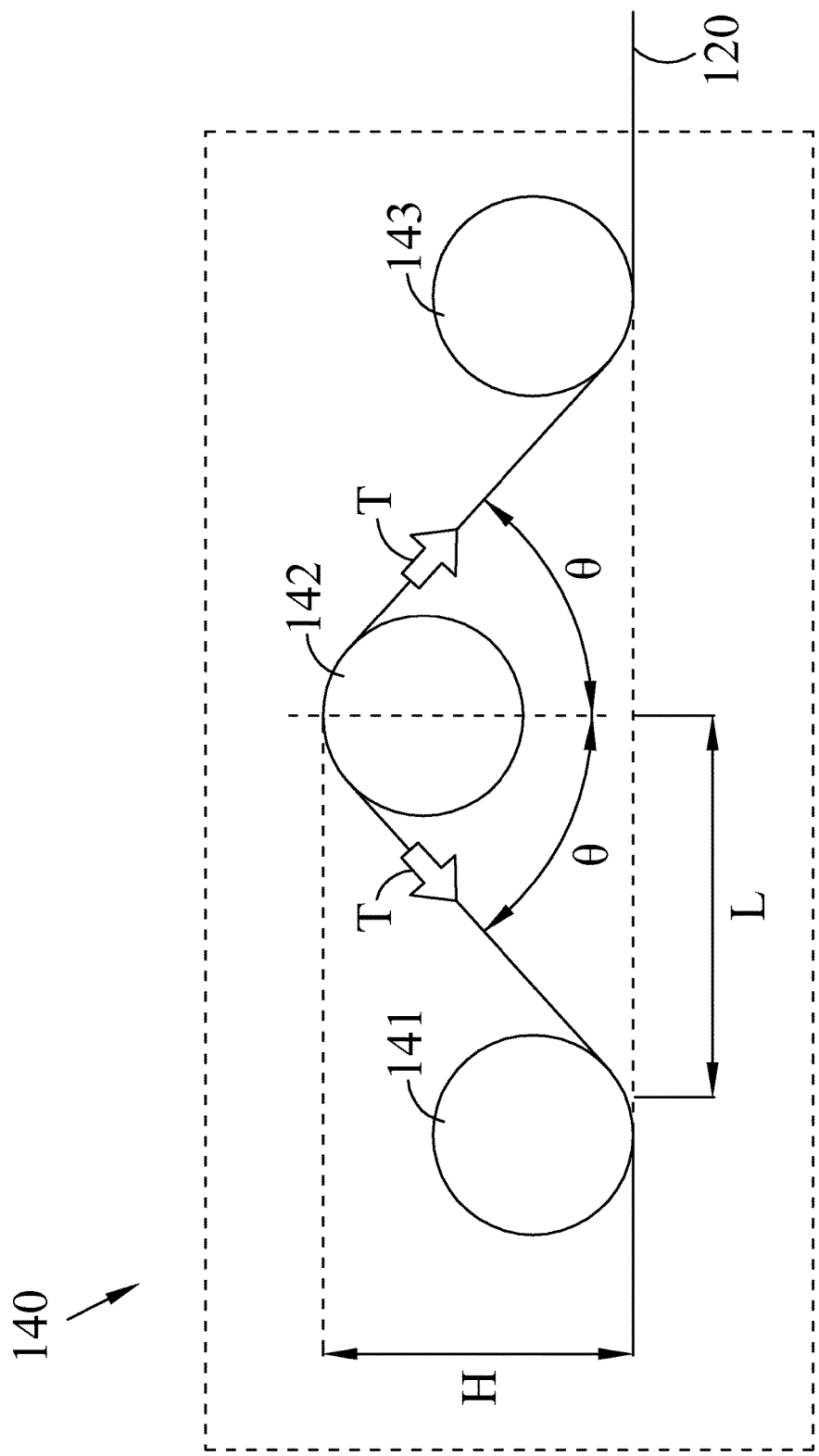
FIG. 2A is a schematic diagram showing the side view of a first tension measurement member of the second embodiment of a rehabilitation system in accordance with the present invention.
Figure 2B:
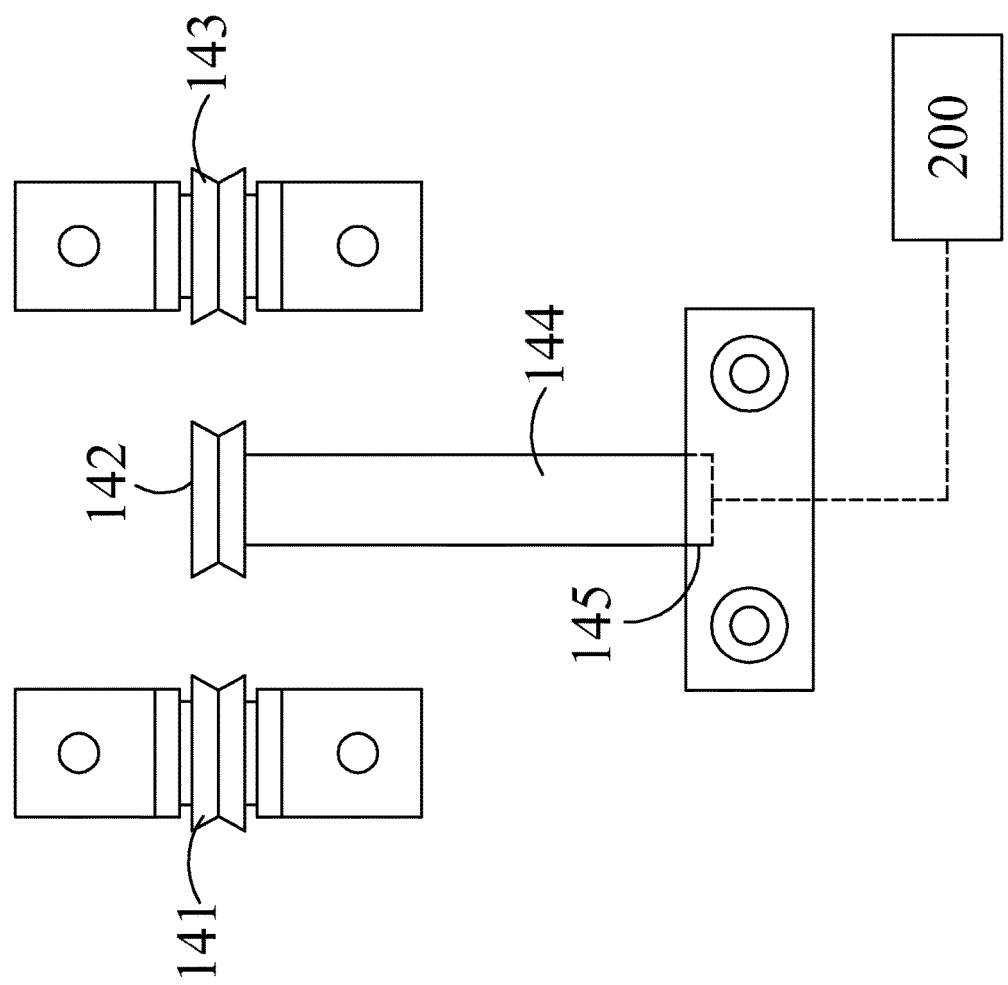
FIG. 2B is a schematic diagram showing the top view of a first tension measurement member of the second embodiment of a rehabilitation system in accordance with the present invention.

Please refer to FIGS. 2A and 2B together which are a schematic diagram of the side view of a first tension measurement member 140 of the second embodiment of a rehabilitation system in accordance with the present invention and a schematic diagram of the top view of a first tension measurement member 140 of the second embodiment of a rehabilitation in accordance with the present invention, respectively. As shown in the figures, the first tension measurement member 140 includes a first roller 141, a second roller 142, and a third roller 143. The first traction line 120 is disposed at a first side of the first roller 141 and the third roller 143 and a second side opposite to the first side of the second roller 142. The second roller 142 is coupled to a cantilever beam 144 with a strain gauge 145 to measure the first tension in the first traction line 120, and the strain gauge 145 outputs a tension signal relating to the first tension to the processor 200.

The embodiment of the first tension measurement member 140 is specifically described herein, but the structure of the first tension measurement member 140 is not limited thereto. The second tension measurement member 150 may have the same or similar structure to the first tension measurement member 140. In this embodiment, the first tension measurement member 140 may include the first roller 141, the second roller 142 and the third rollers 143. The first traction line 120 is bent to pass through the different sides of the first roller 141, second roller 142 and third roller 143. Please refer to FIG. 2A. Specifically, the first roller 141, the second roller 142 and the third roller 143 may be substantially horizontally disposed, such that the first traction line 120 is bent to pass through the different sides of the first roller 141, second roller 142 and third roller 143. In this case, the first traction line 120 applies a downward force $F_{eq}$ to the second roller 142. Here, the tension of the first traction line is a tension T. As the tension T of the first traction line 120 is substantially uniform, and the direction of the tension T at one point on the first traction line 120 is parallel to the direction at the point where the first traction line 120 stretches from. Therefore, the following relationship: $F_{eq}=2T \cos \theta$ can easily be made via the geometric relationships shown in FIG. 2A. As shown in FIG. 2A, $\theta$ is a half of the included angle formed by the first traction line 120 from the first roller 141 to the second roller 142 and then to the third roller 143. The following relation: $\tan \theta = L/H$ is effortlessly determined when the relative positional relationships among the first roller 141, the second roller 142 and the third roller 143 are confirmed. Wherein L and H of the relation shown in FIG. 2A are associated with the parallel and vertical spacing among the first roller 141, the second roller 142 and the third roller 143. Thus, as long as the force $F_{eq}$ is measured, the tension T (i.e., the first tension) in the first traction line 120 can be derived from the other known parameters. Please keep referring to FIG. 2B. In order to achieve the following objective, the second roller 142 is fixed to the cantilever beam 144, and the force $F_{eq}$ of the second roller 142 applied by the first traction line 120 is delivered to the cantilever beam 144. The strain gauge 145 is further disposed on the cantilever beam 144. The strain gauge 145 is able to sense the force applied by the cantilever beam 144. Namely, the aforementioned force $F_{eq}$ is able to be measured. Afterwards, the strain gauge 145 transmits the measured information to the processor 200, and the processor 200 receives the tension T by calculating the force $F_{eq}$ and then analyzes the tension T, such that the stiffness information of the patient's rehabilitation part is obtained.

Figure 3A:
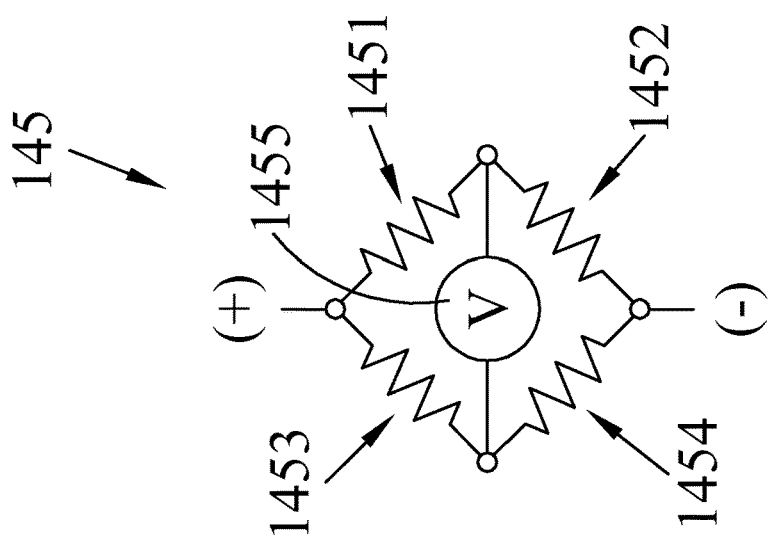
FIG. 3A is a schematic diagram of the function and circuit of a strain gauge of the third embodiment of a rehabilitation system in accordance with the present invention without force applied thereon.
Figure 3A:
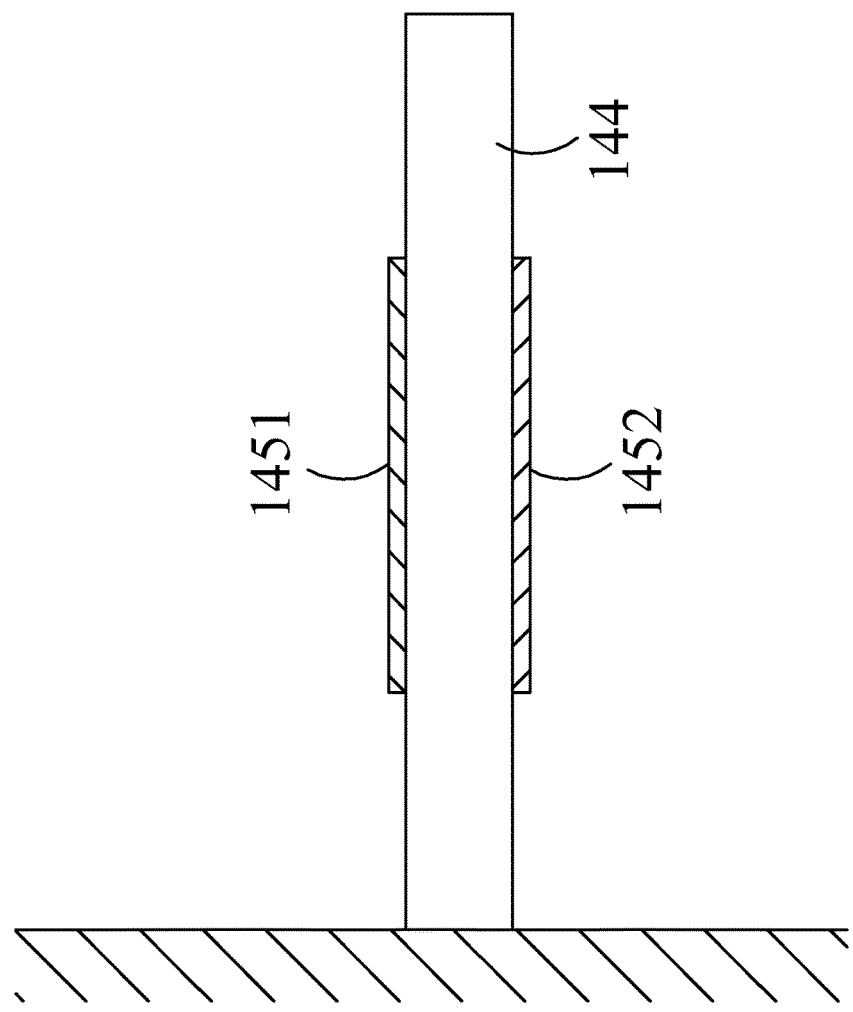
Figure 3B:
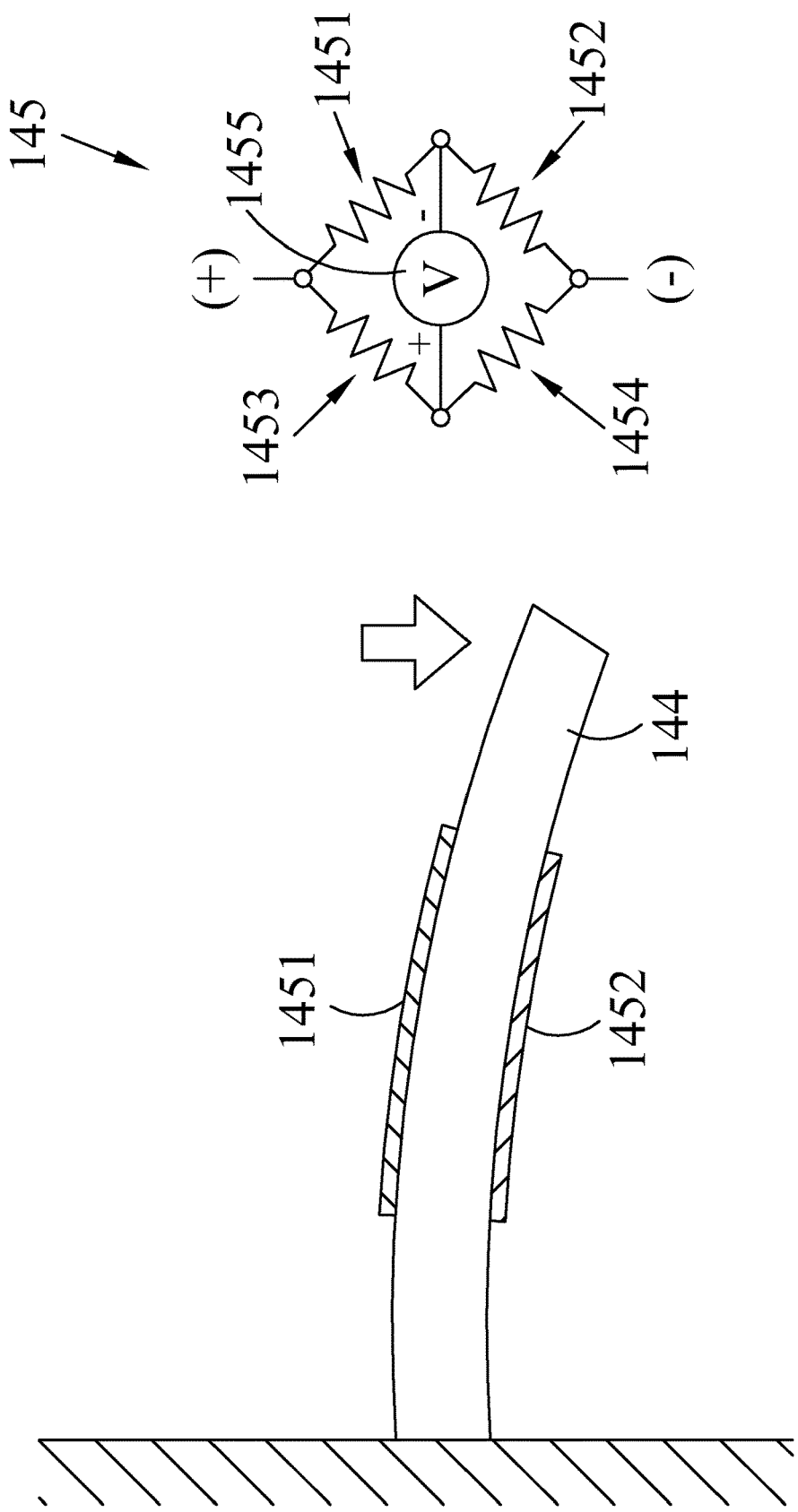
FIG. 3B is a schematic diagram of the function and circuit of a strain gauge of the third embodiment of a rehabilitation system in accordance with the present invention on which force is applied.

Please refer to FIGS. 3A and 3B, where FIG. 3A is a schematic diagram of the function and circuit of a strain gauge of the third embodiment of a rehabilitation system in accordance with the present invention without force applied thereon, and FIG. 3B is a schematic diagram of the function and circuit of a strain gauge of the third embodiment of a rehabilitation system in accordance with the present invention on which force is applied. As shown in the figures, the strain gauge 145 includes a first gauge resistor 1451 and the second gauge resistor 1452, and the first gauge resistor 1451 and the second gauge resistor 1452 are coupled to a bridge circuit to obtain the tension signal relating to the first tension.

Specifically, the strain gauge 145 includes the first gauge resistor 1451 and the second gauge resistor 1452, and the force can be measured and then transformed into electrical signals by combining the first gauge resistor 1451 and the second gauge resistor 1452 with the bridge circuit. The first gauge resistor 1451 and the second gauge resistor 1452 may be a resistor similar to the force sensitive resistor, the resistance value of which becomes large when being stretched and becomes smaller when being compressed. Please refer to the left of FIG. 3A, the first gauge resistor 1451 and the second gauge resistor 1452 are respectively fixed to the upper and lower sides of the cantilever beam 144. Please refer to the right of FIG. 3A, the first gauge resistor 1451 and the second gauge resistor 1452 form the bridge circuit with the other two resistors 1453, 1454 and a voltmeter 1455 simultaneously. Please refer to the left of FIG. 3B, the figure exaggeratedly shows the forced condition of the cantilever beam 144. When the cantilever beam 144 is applied a downward force, the first gauge resistor 1451 is stretched, causing the increase of the resistance value. In contrast, the second gauge resistor 1452 is compressed, causing the decrease of the resistance value. Please refer to the right of FIG. 3B, the changes of this resistance value are reflected in the voltages measured by the voltmeter 1455, so the voltmeter 1455 can transmit the measured voltage signal (i.e., the aforementioned tension signal) to the processor 200, and the processor 200 is able to analyze the force which is applied to the cantilever beam 144. The second tension measurement member 150 may be able to apply the above-mentioned method to measure the applied force provided that the second tension measurement member 150 includes the strain gauge 145.

Figure 4:
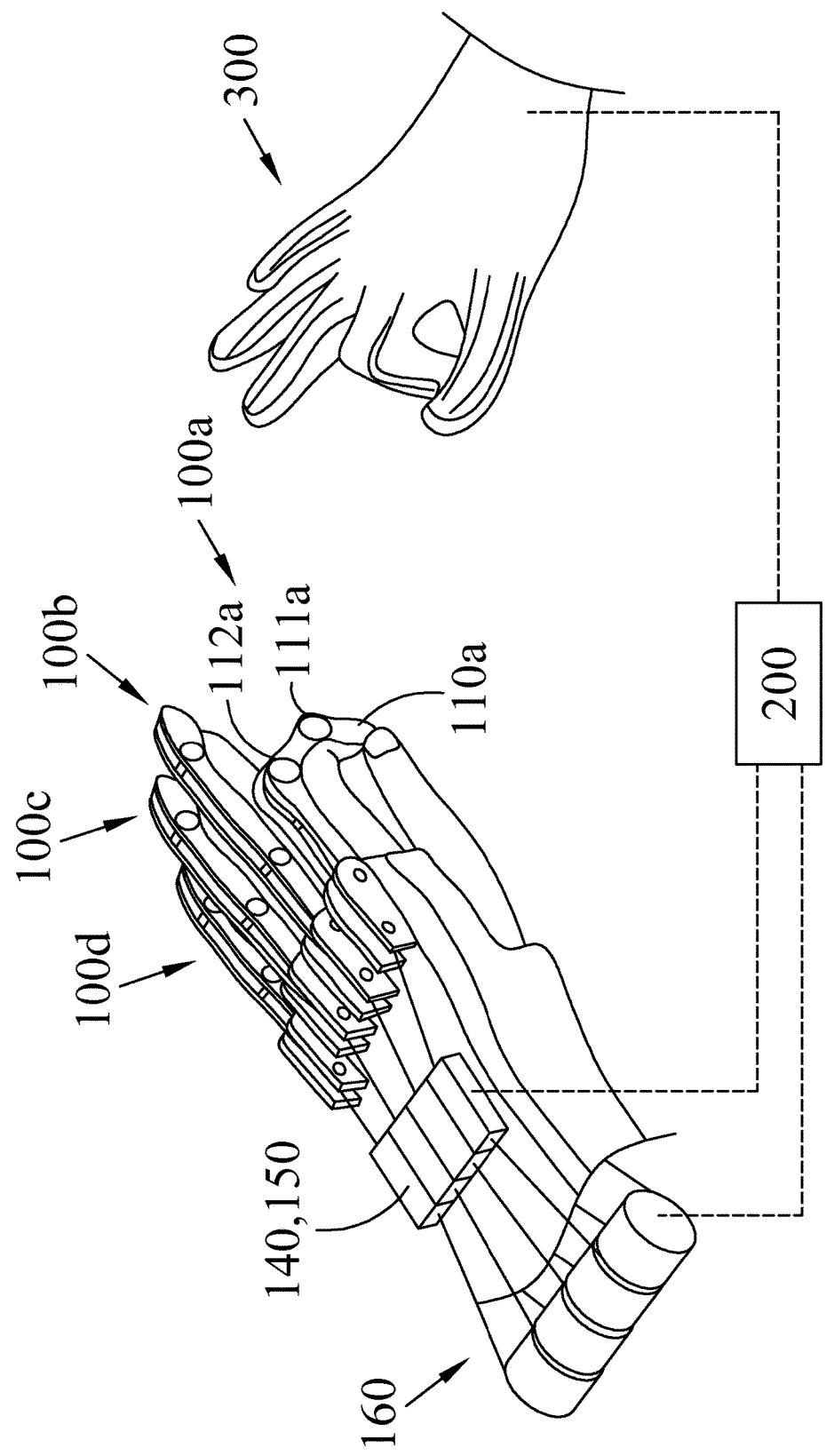
FIG. 4 is a schematic diagram for showing the fourth embodiment of a rehabilitation system of a user wearing a rehabilitation system with stiffness measurement function in accordance with the present invention.

Please refer to FIG. 4 which is a schematic diagram for showing the fourth embodiment of a user wearing a rehabilitation system with stiffness measurement function in accordance with the present invention. In the figure, a rehabilitation system with stiffness measurement function in accordance with the present invention further includes a plurality of rehabilitation units 100a to 100d. The exoskeleton brace 110 of each of the rehabilitation units 100a to 100d includes a plurality of joints, and the first tension measurement member 140 and the second tension measurement member 150 of each of the rehabilitation units 100a to 100d are electrically connected to the processor 200.

For the sake of rehabilitating the human body which has complicated structure and organization, such as hands, a rehabilitation system with stiffness measurement function in accordance with the present invention may include the plurality of the rehabilitation units 100a to 100d. For example, each of the rehabilitation units may correspond to each of the fingers. In this embodiment, the exoskeleton brace 110 of each rehabilitation unit also includes a plurality of joints so as to correspond to the joints of each finger, and each exoskeleton brace 110 is able to drive the finger to move in different specific directions. For example, please refer to the exoskeleton brace 110a shown in FIG. 4, which may include two joints 111a, 112a corresponding to the two joints of the index finger, respectively. Similarly, exoskeleton braces corresponding to the other fingers can be inferred according to the basis. Thus, a rehabilitation system with stiffness measurement function in accordance with the present invention is able to drive the patient's hand to perform more sophisticated rehabilitation activities. At the same time, the first tension measurement member 140 and the second tension measurement member 150 included in the plurality of rehabilitation units 100a to 100d are all electrically connected to the processor 200. Thus, the processor 200 is able to obtain the various situations of stiffness of each of the patient's fingers in each specific movement direction by analyzing the tension in the first traction line 120 and the second traction line 130 included in each of the plurality of rehabilitation units 100a to 100d.

Please refer to FIG. 4, again. In the figure, a rehabilitation system with stiffness measurement function in accordance with the present invention may further include a motion capture glove 300 electrically connected to the processor 200 and outputting a motion signal to the processor 200. The processor 200 is electrically connected to each driving motor 160 of the plurality of rehabilitation units 100a to 100d, and then drives each driving motor 160 of the plurality of rehabilitation units 100a to 100d according to the motion signal.

In clinical practice, many of the symptoms such as paralysis resulted from a stroke belong to the hemiplegia. In other words, patients may only need to rehabilitate the hand suffered from the paralysis, and the other hand can still freely move. In this case, the patient is able to rehabilitate by using the plurality of rehabilitation units 100a to 100d, the processor 200 and the motion capture glove 300 disclosed in the present invention. For example, when the patient's left hand needs to rehabilitate and right hand is normal, the patient can wear the exoskeleton braces 110 of the plurality of the rehabilitation units 100a to 100d of the present invention on left hand, and the motion capture glove 300 on the right hand. Thus, the motion capture glove 300 captures the activities of the patient's right hand, and the motion signals are generated and transmitted to the processor 200 accordingly. Then, the motion capture glove 300 drives the driving motor 160 of each of the plurality of the rehabilitation units 100a to 100d according to the motion signals. As a result, the precise rehabilitation can be performed without setting complicated commands. While performing rehabilitation with the rehabilitation system of this embodiment of the present invention, the patient only need to intuitively move one hand and the other hand will be moved correspondingly.

Figure 5:
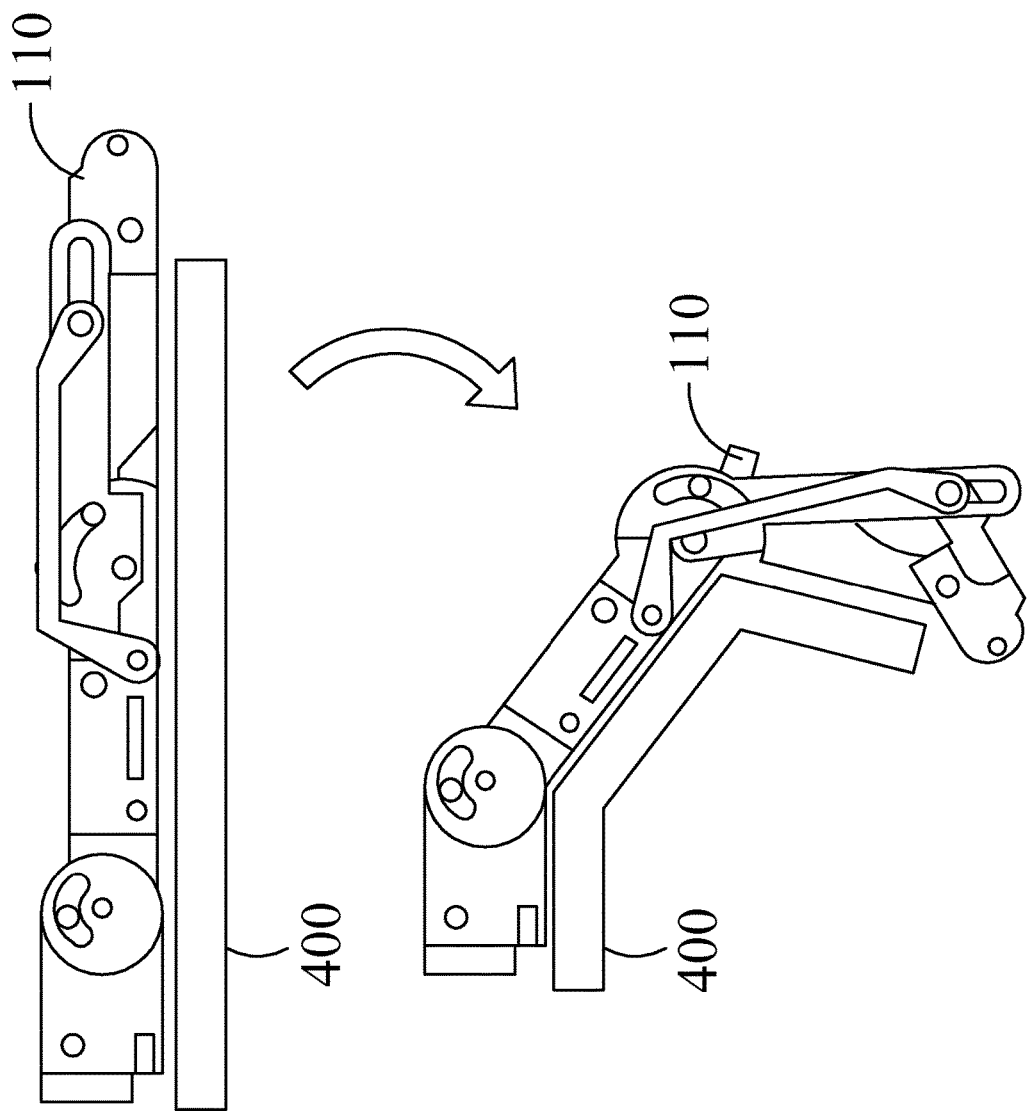
FIG. 5 is a layout diagram for showing a test of a rehabilitation system with stiffness measurement function in accordance with the present invention.
Figure 6A:
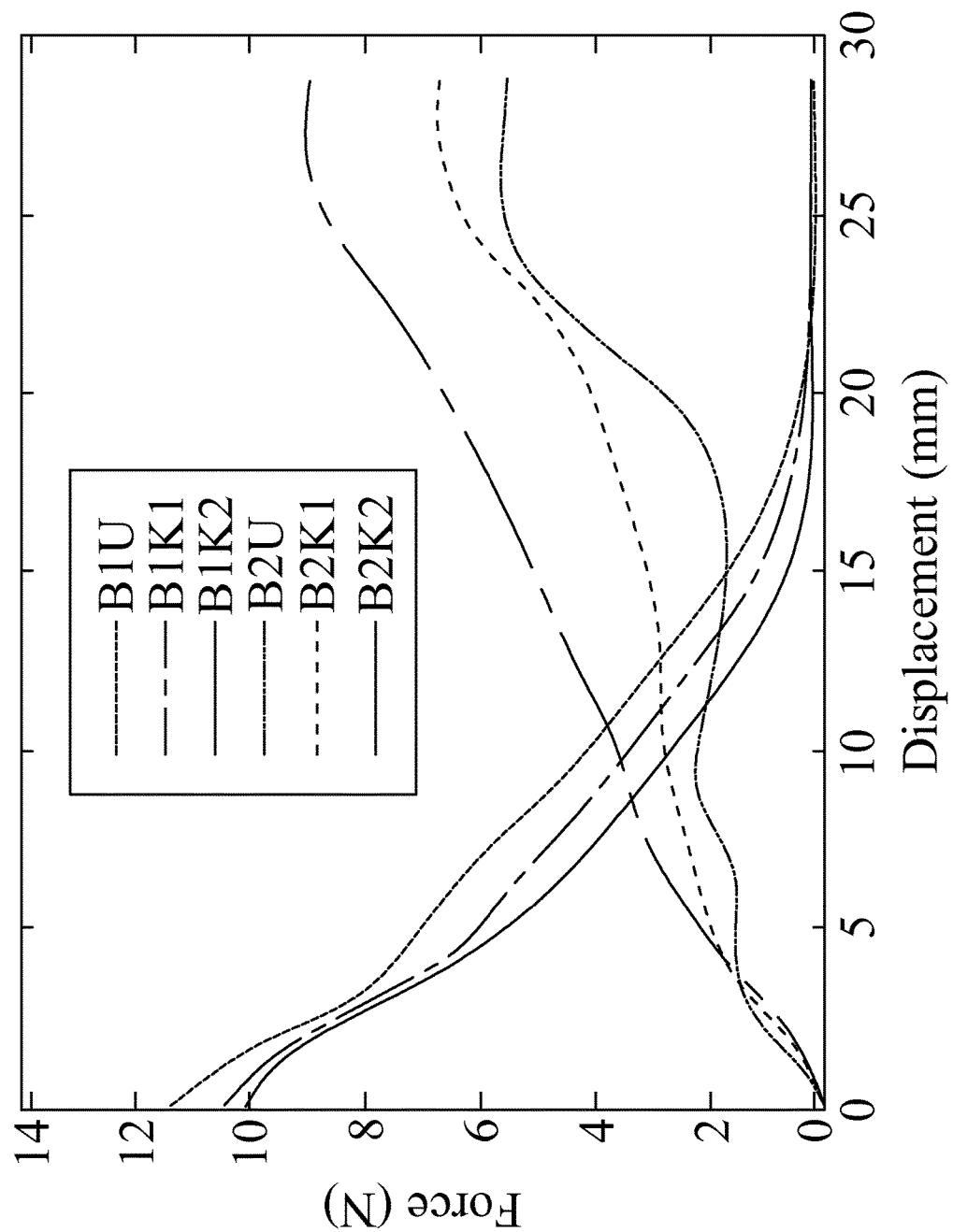
FIG. 6A shows the test result when an exoskeleton brace of a rehabilitation system with stiffness measurement function in accordance with the present invention is bending.
Figure 6B:
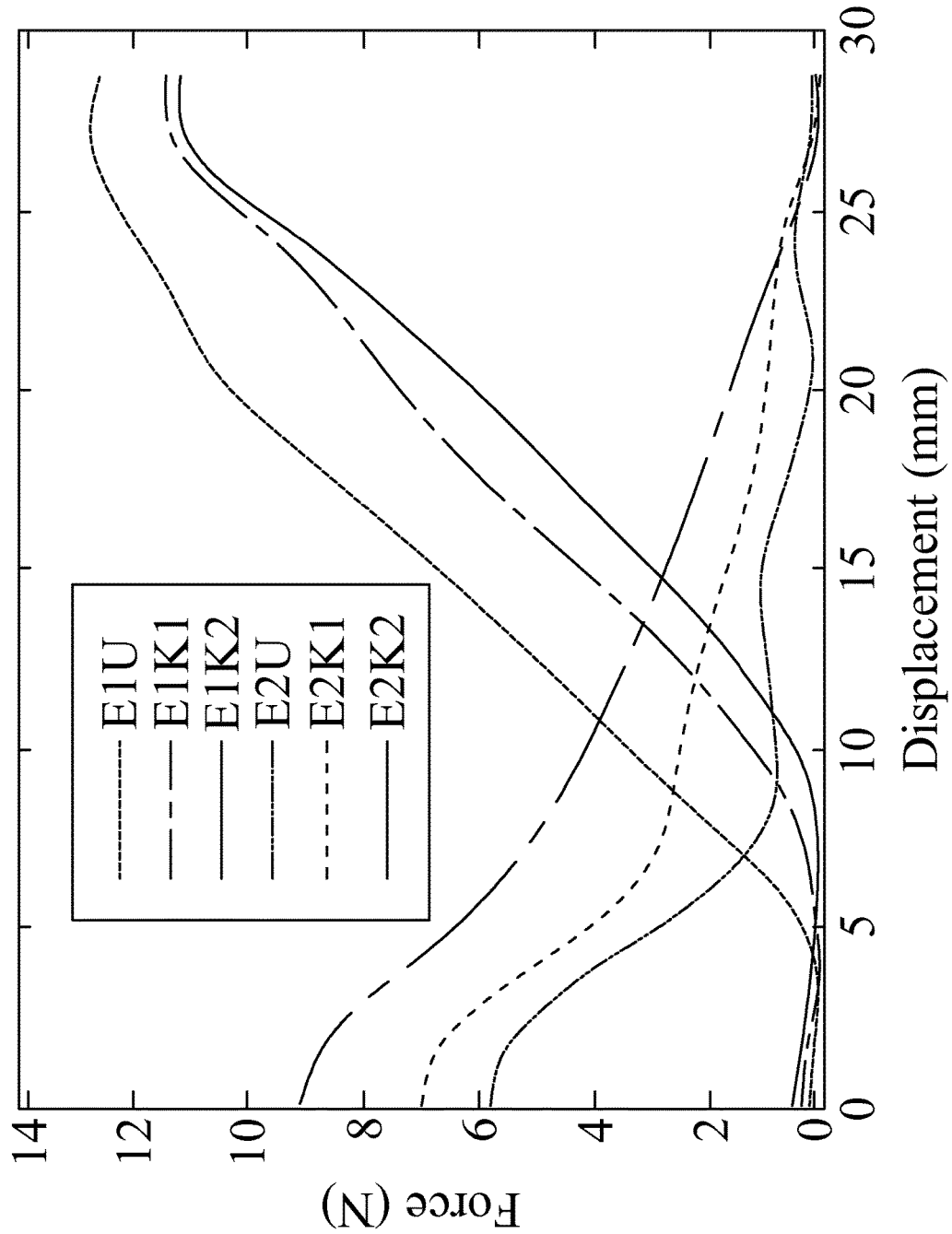
FIG. 6B shows the test result when an exoskeleton brace of a rehabilitation system with stiffness measurement function in accordance with the present invention is stretching.

Please refer to FIG. 5 which is a layout diagram for showing a test of a rehabilitation system with stiffness measurement function in accordance with the present invention. In the following tests, the exoskeleton brace 110 of the present invention is combined with test samples 400, and different test samples 400 have different elastic constants K1 and K2, wherein K2 is greater than K1. Elastic constants of the test sample 400 correspond to the various situations of stiffness of the patient's rehabilitation part moving in a specific direction. Please refer to FIG. 6A and FIG. 6B which show the test results when an exoskeleton brace of a rehabilitation system with stiffness measurement function in accordance with the present invention is bending and stretching, respectively. In the figures, the horizontal axis represents the distance of the driving motor 160 stretching the first traction line 120 or the second traction line 130. The vertical axis represents the tension in lines (in the first traction line 120 or the second traction line 130). In FIG. 6A and FIG. 6B, the graph of the first numeral is "B", which means the measurement when the exoskeleton brace 110 is bending. "E" indicates the measurement when the exoskeleton brace 110 is stretching. The second numeral "1" indicates the tension measured in the first traction line 120, and the second numeral "2" indicates the tension measured in the second traction line 130. The last numeral "U" denotes the measurement of the exoskeleton brace 110 without being coupled to the test sample 400, the last numeral "K1" indicates the measurement of the exoskeleton brace 110 coupling to the test sample 400 having the elastic constant K1, and the last numeral "K2" indicates the measurement of the exoskeleton brace 110 coupling to the test sample 400 having the elastic constant K2. For example, the graph B1U denotes the tension measured in the first traction line 120 when the exoskeleton brace 110 bends without being coupled to the test sample 400, and the graph E2K2 denotes the tension measured in the second traction line 130 when the exoskeleton brace 110 stretches and is coupled to the test sample 400 having the elastic constant K2. The figures show that even though the distances stretched by the driving motor 160 are the same, with the differences of the test sample's 400 elastic constants, tensions that measured with different elastic constants of samples in the first traction line 120 and the second traction line 130 may have obvious differences. Besides, the measured force differences of the measurement results obtained from the test for the test sample 400 having the elastic constant K2 and the uncoupled test are greater than that obtained from the test for the test sample 400 having the elastic constant K1 and the uncoupled test. It is noted that the distance stretched by the driving motor 160 and the relationship between the first traction line 120 and the second traction line 130 are not a monotonic function, but have different variation tendencies with different mechanical means.

Thus, according to the above test results, the processor 200 of the present invention may store unload data measured when the exoskeleton brace 110 is not coupled to the rehabilitation part, and the processor 200 compares the first tension and the second tension with the unload data to obtain the stiffness information of the rehabilitation part in the specific moving direction.

Since the force differences of the measurement results obtained from the test for the test sample 400 having the greater elastic constants and the uncoupled test are all larger than the force differences obtained from the test for the test sample 400 having the smaller elastic constants and the uncoupled test, the processor 200 is able to store the measured unload data (such as the graphs B1U and B2U in FIG. 6A, and the graphs E1U and E2U in FIG. 6B) as a benchmark or baseline data when the exoskeleton brace 110 is not coupled to the rehabilitation part, such that the tension information derived from the rehabilitation system of the present invention is able to be compared with the unload data stored in the processor 200 when the patient is rehabilitating. The greater the force differences between the tension information and the unload data are, the more stiff the patient's rehabilitation part is. Further, since the distance varies with the stretch of the driving motor 160, the force difference value is able to be quantified as various situations of the stiffness of the rehabilitation part in the specific distance according to the physician's professional judgment. For example, physicians can, through the analysis of clinical data, define that when the stretching distance of the driving motor 160 is 10 mm and has force difference of 0.5 N from the unload data, the rehabilitation part has the stiffness st1 in the specific moving direction. When the stretching of the driving motor 160 is 15 mm and has force difference of 1 N from the unload data, the rehabilitation part has the defined stiffness st2. Once these definitions are given by the physician, it can be adopted to the same or similar rehabilitation treatment. Thus, the rehabilitation system of the present invention will enable physicians to quickly have the various situations of the patient's rehabilitation in hand.

In addition, when the different test samples 400 are repeatedly tested, the test sample 400 having the same elastic constant shown in FIG. 6A or FIG. 6B always has the same or similar curved line, and the different elastic constants indicate the various situations of stiffness. Therefore, the processor 200 of the rehabilitation system of the present invention is able to further store a tension database corresponding to the tension variety in the first traction line and the second traction line at the various situations of stiffness (elastic constants). The processor 200 is able to analyze the first tension and the second tension by table look-up or interpolation according to the upload data and the tension database to obtain the stiffness information of the rehabilitation part in the specific moving direction. This database can be pre-stored in the processor 200 of the rehabilitation system of the present invention while producing the rehabilitation system, and can be updated while the software version of the processor 200 is updating in the future.

Figure 7:
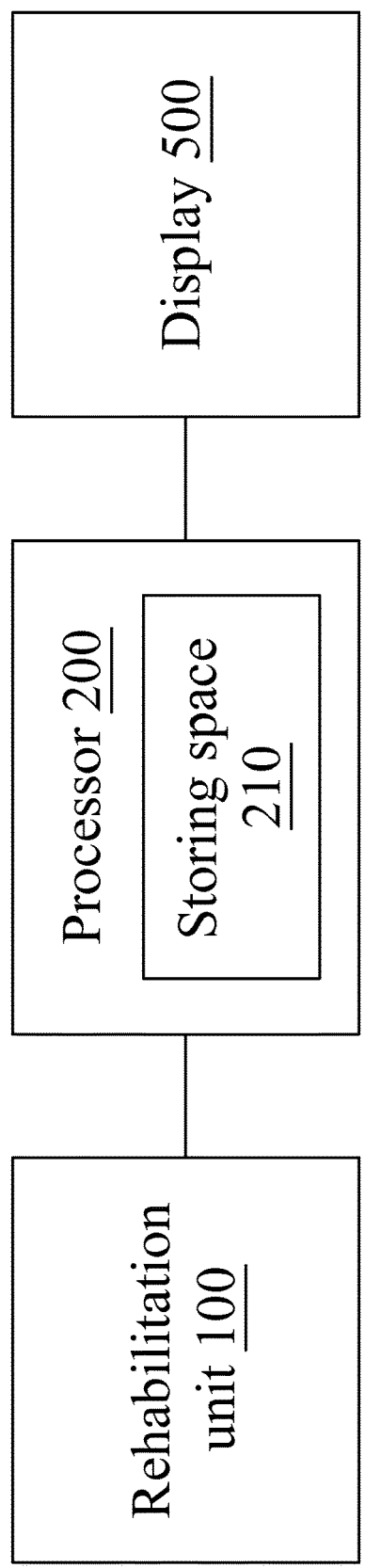
FIG. 7 is a block diagram of the fifth embodiment of a rehabilitation system with stiffness measurement function in accordance with the present invention.

Please refer to FIG. 7 which is a block diagram of the fifth embodiment of a rehabilitation system with stiffness measurement function in accordance with the present invention. In the figure, the processor 200 includes a storing space 210, and the measured stiffness information of the rehabilitation part in the specific moving direction is stored in the storing space 210.

In order to make it easier for physicians and patients to understand the current progress of rehabilitation, the stiffness information measured by the rehabilitation system of the present invention is able to be stored in the storing space 210 of the processor 200. In addition to the current stiffness information, the previous stiffness information can be retrieved from the storing space 210 as well. Thus, the physician only need to compares the current stiffness information with the previous one, the condition of the current rehabilitation part can be obtained effortlessly, and the assessment to how the effectiveness of the current rehabilitation treatments goes is thereby made.

Please refer to FIG. 7, again. In the figure, a display 500 is electrically connected to the processor 200, receives the stiffness information from the processor, and presents information relating to the stiffness information Specifically, the display 500 may be a liquid crystal display, but is not limited thereto. In order to make the physician and the patient to quickly understand the current stiffness of the rehabilitation part, the processor 200 of the rehabilitation system of the present invention is electrically connected to the display 500, and transmits information signals regarding the various situations of stiffness to the display 500, such that the display 500 is able to display the stiffness information on the screen. For example, the processor 200 may integrate the current measured stiffness information and the previous one into a tendency chart, and then display the tendency chart on the display 500, so that the physician and patient are absolutely clear to know how the effectiveness of the current rehabilitation goes.

While the means of specific embodiments in present invention has been described by reference drawings, numerous modifications and variations could be made thereto by those skilled in the art without departing from the scope and spirit of the invention set forth in the claims. The modifications and variations should in a range limited by the specification of the present invention.

What is claimed is:

1. A rehabilitation system with stiffness measurement function, comprising:
a rehabilitation unit, comprising:
an exoskeleton brace configured to be coupled to a rehabilitation part of a user;
a first traction line, coupled to an end of the exoskeleton brace;
a second traction line, coupled to the end of the exoskeleton brace;
a first tension measurement member, configured to enable the first traction line to pass therethrough;
a second tension measurement member, configured to enable the second traction line to pass therethrough; and
a driving motor, coupled to the first traction line and the second traction line, wherein when the driving motor rotates in a first driving direction, the exoskeleton brace is driven by the first traction line to move in a first direction, and when the driving motor rotates in a second driving direction, the exoskeleton brace is driven by the second traction line to move in a second direction opposite to the first direction; and
a processor, electrically connected to the first tension measurement member and the second tension measurement member,
wherein when the exoskeleton brace of the rehabilitation unit moves, the first tension measurement member and the second tension measurement member measure a first tension in the first traction line and a second tension in the second traction line, respectively; the first tension measurement member and the second tension measurement member provide the first tension and the second tension to the processor, and the processor analyzes the first tension and the second tension to obtain stiffness information of the rehabilitation part in a specific moving direction; and
the first tension measurement member comprises a first roller, a second roller, and a third roller; the first traction line is disposed at a first side of the first roller and the third roller and a second side opposite to the first side of the second roller, the second roller is coupled to a cantilever beam with a strain gauge to measure the first tension in the first traction line, and the strain gauge outputs a tension signal relating to the first tension to the processor; wherein the processor stores unload tension data measured when the exoskeleton brace is not coupled to the rehabilitation part, and the processor compares the first tension and the second tension with the unload data to obtain the stiffness information of the rehabilitation part in the specific moving direction.

2. The rehabilitation system of claim 1, wherein the strain gauge comprises a first gauge resistor and a second gauge resistor, and the first gauge resistor and the second gauge resistor are coupled to a bridge circuit to obtain the tension signal relating to the first tension.

3. The rehabilitation system of claim 2, further comprising:
a motion capture glove, electrically connected to the processor and outputting a motion signal to the processor,
wherein the processor is electrically connected to the driving motor of each of the rehabilitation units and controls the driving motor of each of the rehabilitation units according to the motion signal.

4. The rehabilitation system of claim 3, wherein the processor further stores a tension database corresponding to a variety of tension values in the first traction line and the second traction line at various situations of stiffness, and the processor analyzes the first tension and the second tension by table look-up or interpolation according to an upload data and the tension database to obtain the stiffness information of the rehabilitation part in the specific moving direction.

5. The rehabilitation system of claim 1, further comprising:
a plurality of the rehabilitation units, the exoskeleton brace of each of the rehabilitation units comprising a plurality of joints, and the first tension measurement member and the second tension measurement member of each of the rehabilitation units electrically connected to the processor.

6. The rehabilitation system of claim 1, wherein the processor comprises a storing space, and the measured stiffness information of the rehabilitation part in the specific moving direction is stored in the storing space.

7. The rehabilitation system of claim 1, further comprising:
a display, electrically connected to the processor, receiving the stiffness information from the processor, and presenting information relating to the stiffness information.

* * * * *